US012653500B2

(12) United States Patent
Shimizu et al.

(10) Patent No.: US 12,653,500 B2
(45) Date of Patent: Jun. 16, 2026

(54) ULTRASOUND CATHETER AND ULTRASOUND CATHETER SYSTEM

(71) Applicant: TERUMO KABUSHIKI KAISHA, Tokyo (JP)

(72) Inventors: Katsuhiko Shimizu, Fujinomiya (JP); Hiroyuki Ishihara, Tokyo (JP); Yasukazu Sakamoto, Hiratsuka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 770 days.

(21) Appl. No.: 17/943,513

(22) Filed: Sep. 13, 2022

(65) Prior Publication Data

US 2023/0000464 A1     Jan. 5, 2023

Related U.S. Application Data

(63) Continuation of application No. PCT/JP2021/008616, filed on Mar. 5, 2021.

(30) Foreign Application Priority Data

Mar. 13, 2020     (JP) ................................. 2020-043662

(51) Int. Cl.
 *A61B 8/00* (2006.01)
 *A61M 25/00* (2006.01)

(52) U.S. Cl.
 CPC ............ *A61B 8/4461* (2013.01); *A61B 8/445* (2013.01); *A61M 2025/004* (2013.01); *A61M 2205/103* (2013.01)

(58) Field of Classification Search
 CPC ................................. A61B 8/12; A61B 8/4461
 See application file for complete search history.

(56) References Cited

U.S. PATENT DOCUMENTS 4,856,529 A * 8/1989 Segal ...................... A61B 8/445
                                                             600/455
5,456,258 A * 10/1995 Kondo ................... A61B 8/445
                                                             600/463

(Continued)

FOREIGN PATENT DOCUMENTS

CN         105920717 A * 9/2016 .......... A61M 39/225
JP         2002253551 A * 9/2002

(Continued)

OTHER PUBLICATIONS

International Search Report (PCT/ISA/210) with translation and Written Opinion (PCT/ISA/237) mailed on Apr. 27, 2021, by the Japan Patent Office as the International Searching Authority for International Application No. PCT/JP2021/008616. (9 pages).

*Primary Examiner* — William R Carpenter
(74) *Attorney, Agent, or Firm* — .Buchanan Ingersoll & Rooney PC

(57) ABSTRACT

An ultrasound catheter and an ultrasound catheter system that can acquire an image of an observation target with high accuracy when inserted into a large inner lumen. An ultrasound catheter includes: an outer sheath having an accommodation lumen; an inner sheath that can move along an axis; a drive shaft that can rotate in the inner sheath and the outer sheath; and a transducer that is disposed in the accommodation lumen and fixed to a distal end of the drive shaft. The outer sheath includes a first bent portion bent and shaped in advance at a predetermined angle on a proximal side of a most distal end of the accommodation lumen, and a first tubular portion and a second tubular portion positioned on a distal side of the first bent portion and on the proximal side of the most distal end of the accommodation lumen.

20 Claims, 7 Drawing Sheets

(56)            References Cited

U.S. PATENT DOCUMENTS

| | | | | |
|---|---|---|---|---|
| 5,507,294 | A * | 4/1996 | Lum | A61B 8/06 600/459 |
| 5,842,994 | A * | 12/1998 | TenHoff | A61B 8/12 600/468 |
| 12,097,070 | B2 * | 9/2024 | Shimizu | A61B 8/445 |
| 2013/0023770 | A1 | 1/2013 | Courtney et al. | |
| 2014/0371598 | A1 * | 12/2014 | Okubo | A61M 25/0662 600/467 |
| 2016/0143616 | A1 * | 5/2016 | Okubo | A61M 39/10 600/467 |
| 2016/0158502 | A1 | 6/2016 | Kume et al. | |
| 2017/0049511 | A1 | 2/2017 | Uhm et al. | |
| 2017/0333001 | A1 * | 11/2017 | Sakaguchi | A61B 8/461 |
| 2018/0214670 | A1 * | 8/2018 | Sakaguchi | A61M 25/0144 |
| 2021/0007580 | A1 | 1/2021 | Shimizu et al. | |

FOREIGN PATENT DOCUMENTS

| | | | | |
|---|---|---|---|---|
| JP | 6073295 | B2 | 1/2017 | |
| JP | 2017525519 | A | 9/2017 | |
| WO | WO-9211055 | A1 * | 7/1992 | A61M 25/0029 |
| WO | 2019188658 | A1 | 10/2019 | |

* cited by examiner

FIG. 4A        FIG. 4B
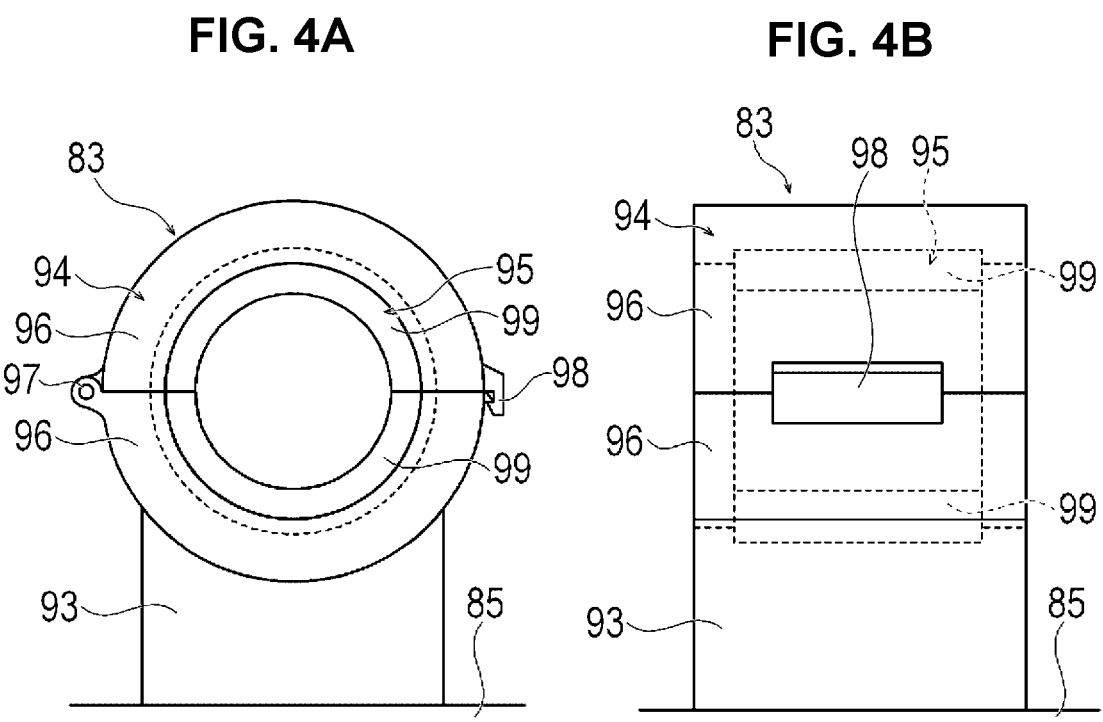
FIG. 5
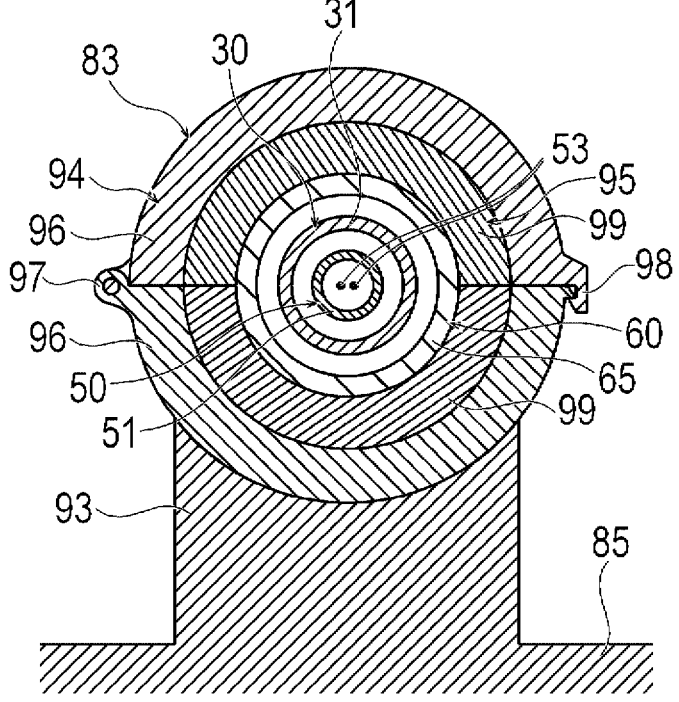

ULTRASOUND CATHETER AND ULTRASOUND CATHETER SYSTEM

CROSS-REFERENCES TO RELATED APPLICATIONS

This application is a continuation of International Application No. PCT/JP2021/008616 filed on Mar. 5, 2021, which claims priority to Japanese Application No. 2020-043662 filed on Mar. 13, 2020, the entire content of both of which is incorporated herein by reference.

TECHNOLOGICAL FIELD

The present disclosure generally relates to an ultrasound catheter and an ultrasound catheter system that acquire an image by being inserted into an inner lumen such as a heart or a blood vessel.

BACKGROUND DISCUSSION

When a lesion is examined from a heart, a blood vessel, or the like, an ultrasound catheter that is inserted into an inner lumen of a living body and acquires an image by using ultrasound is used (for example, see Japanese Patent No. 6,073,295). The ultrasound catheter includes a transducer for transmitting and receiving ultrasound, a drive shaft that rotates the transducer, and a sheath that rotatably accommodates the transducer and the drive shaft. The transducer is rotationally driven by the drive shaft in the sheath to transmit and receive the ultrasound, and acquires an image in the living body.

An inner lumen of a blood vessel of a heart, a lower limb, or an abdomen is larger than that of a blood vessel such as a coronary artery. In observation with an ultrasound catheter in the large inner lumen, as a distance from the ultrasound transducer to an observation target increases, the ultrasound spreads, and therefore observation of the observation target becomes relatively difficult. Therefore, an ultrasound catheter that can acquire a relatively highly accurate image even in a heart, a blood vessel of a lower limb or an abdomen, or the like having a large inner lumen is desired.

SUMMARY

An ultrasound catheter and an ultrasound catheter system are disclosed that can acquire an image of an observation target with relatively high accuracy even when the ultrasound catheter and the ultrasound catheter system are inserted into a relatively large inner lumen.

An ultrasound catheter is disclosed that includes: an outer sheath in which an accommodation lumen configured to extend from a proximal end to a distal end is formed; an inner sheath configured to move in the accommodation lumen along an axis of the outer sheath; a drive shaft configured to rotate in the inner sheath and/or the outer sheath; and a transducer that is disposed on a distal side of the inner sheath in the accommodation lumen, and that is fixed to a distal end of the drive shaft, in which the outer sheath includes a bent portion that is bent and shaped in advance at a predetermined angle on a proximal side of a most distal end of the accommodation lumen, and a tubular portion that has an axis having a radius of curvature larger than a radius of curvature of an axis of the bent portion, the tubular portion being positioned on a distal side of the bent portion and on the proximal side of the most distal end of the accommodation lumen, and the outer sheath is rotatable with respect to the inner sheath.

An ultrasound catheter system is disclosed that includes an ultrasound catheter; and a drive device configured to drive the ultrasound catheter, in which the ultrasound catheter includes an outer sheath in which an accommodation lumen configured to extend from a proximal end to a distal end is formed, an inner sheath configured to move in the accommodation lumen along an axis of the outer sheath, a drive shaft configured to rotate in the inner sheath and/or the outer sheath, a transducer that is disposed on a distal side of the inner sheath in the accommodation lumen, and that is fixed to a distal end of the drive shaft, a first housing to which a proximal portion of the outer sheath is fixed and through which the drive shaft and the inner sheath pass, and a second housing that is disposed on a proximal side of the first housing, to which a proximal portion of the inner sheath is fixed, and configured to rotatably hold the drive shaft, in which the outer sheath includes a bent portion that is bent and shaped in advance at a predetermined angle on a proximal side of a most distal end of the accommodation lumen, and a tubular portion that has an axis having a radius of curvature larger than a radius of curvature of an axis of the bent portion, the tubular portion being positioned on a distal side of the bent portion and on the proximal side of the most distal end of the accommodation lumen, in which the outer sheath is rotatable of the inner sheath, in which the drive device includes a proximal side support portion configured to support the second housing, a movement portion configured to move the proximal side support portion in an axial direction, a drive unit configured to transmit a rotational force to the drive shaft, and a distal side support portion configured to rotatably support the first housing.

Since the outer sheath is rotated with respect to the inner sheath, the ultrasound catheter configured as described above can freely adjust a distance and an angle of the transducer, which is in the accommodation lumen positioned in the tubular portion on the distal side of the bent portion, with respect to an observation target. Therefore, the ultrasound catheter can acquire an image of the observation target with relatively high accuracy even when the ultrasound catheter is inserted into a relatively large inner lumen.

Since the first housing supported by a distal side support portion is rotatable, by rotating the outer sheath fixed to the first housing with respect to the inner sheath, the ultrasound catheter system configured as described above can freely adjust the distance and the angle of the transducer, which is in the accommodation lumen positioned in the tubular portion on the distal side of the bent portion, with respect to the observation target. Therefore, the ultrasound catheter system can acquire an image of the observation target with relatively high accuracy even when the ultrasound catheter system is inserted into a relatively large inner lumen.

An axis of the tubular portion may be linear. Accordingly, since the transducer to be moved in the accommodation lumen is moved linearly, obtained images can be rather easily connected in the axial direction, and a relatively highly accurate three-dimensional image can be acquired.

The outer sheath may include may include two or more bent portions at different positions in an axial direction. Accordingly, as compared with a case where the outer sheath includes only one bent portion, it is rather easy to dispose the transducer at a desirable position.

At least one of the two or more bent portions may be bent toward a side opposite to another of the two or more bent portions. Accordingly, the distal portion of the outer sheath can be disposed at a position offset from the proximal portion of the outer sheath while having a shape close to parallel to the proximal portion of the outer sheath. Therefore, the distal portion of the outer sheath is rather easily disposed along a wall of an inner lumen of a heart or an inner lumen such as a blood vessel. Therefore, the transducer that pulls back along the axis can be disposed at a desirable position with respect to the observation target in a relatively large range of the outer sheath in the axial direction.

The ultrasound catheter may include the two or more portions bent toward the same side. Accordingly, an angle of each bent portion of the outer sheath can be reduced. Therefore, it is possible to reduce a load on the drive shaft that is movable in an axial direction while being rotated in the bent portion, and to help prevent occurrence of a rotation failure or a failure in movement in the axial direction. Further, since the outer sheath can be largely bent as a whole by the two or more bent portions, orientation is facilitated.

The transducer may be configured to move in the accommodation lumen in an axial direction beyond the bent portion. Accordingly, the transducer can acquire an image of an internal structure of a living body positioned in a relatively large range beyond the bent portion in an axial direction of the accommodation lumen.

A bending angle of the axis of the bent portion may be 5° to 20°. When the bending angle is not too small, it is relatively easy to set an offset amount of the outer sheath to a desirable value. Further, when the bending angle is not too large, rotation and movement in the axial direction of the drive shaft, which moves in the axial direction while being rotated in a state of being bent in the bent portion, are less likely to be hindered.

The outer sheath may include a proximal side tubular portion on a proximal side of a bent portion on a most proximal side, and a distal portion length, which is a length from the bent portion on a most proximal side to a most distal end of the outer sheath along a linear reference line where an axis of at least a distal portion of the proximal side tubular portion is positioned, may be, for example, 20 mm to 150 mm. Accordingly, a length of a portion offset with respect to the proximal side tubular portion can be set, for example, to a length appropriate for observation in a heart or a blood vessel having a relatively large inner lumen.

The outer sheath may include the proximal side tubular portion on the proximal side of the bent portion on the most proximal side, and an offset amount, which is a length from the linear reference line where the axis of at least the distal portion of the proximal side tubular portion is positioned to an axis of a portion farthest in a direction perpendicular to the reference line of a portion on a distal side of the bent portion of the outer sheath on the most proximal side, may be, for example, 5 mm to 30 mm. Since the offset amount has an appropriate magnitude, it is relatively easy to bring the outer sheath close to the observation target in the heart or the blood vessel having the large inner lumen.

An ultrasound catheter is disclosed, comprising: an outer sheath, the outer sheath includes an accommodation lumen configured to extend from a proximal end to a distal end of the outer sheath; a drive shaft configured to move in an axial direction of the outer sheath; a transducer fixed to a distal end of the drive shaft; the outer sheath includes a bent portion, the bent portion being bent and shaped in advance at a predetermined angle on a proximal side of a most distal end of the accommodation lumen, and a tubular portion having a linear axis, the tubular portion being positioned on a distal side of the bent portion and on the proximal side of the most distal end of the accommodation lumen; the outer sheath is rotatable with respect to the drive shaft; and wherein the transducer is configured to move in the accommodation lumen in the axial direction of the outer sheath beyond the bent portion.

BRIEF DESCRIPTION OF THE DRAWINGS

FIGS. 2A and 2B show cross-sectional views of the ultrasound catheter before a transducer is pulled back, in which FIG. 2A shows a distal portion and FIG. 2B shows a proximal portion.

FIGS. 4A and 4B show views of a holding portion of a drive device, in which FIG. 4A is a front view, and FIG. 4B is a side view.

FIG. 5 is a cross-sectional view showing a state where the ultrasound catheter is supported by a distal end support portion of the drive device.

FIGS. 6A and 6B show cross-sectional views showing a state where the transducer of the ultrasound catheter is pulled back, in which FIG. 6A shows the distal portion and FIG. 6B shows the proximal portion.

FIGS. 9A-9C show plan views showing modifications of the ultrasound catheter, in which FIG. 9A shows a first modification, FIG. 9B shows a second modification, and FIG. 9C shows a third modification.

DETAILED DESCRIPTION

Figure 1:
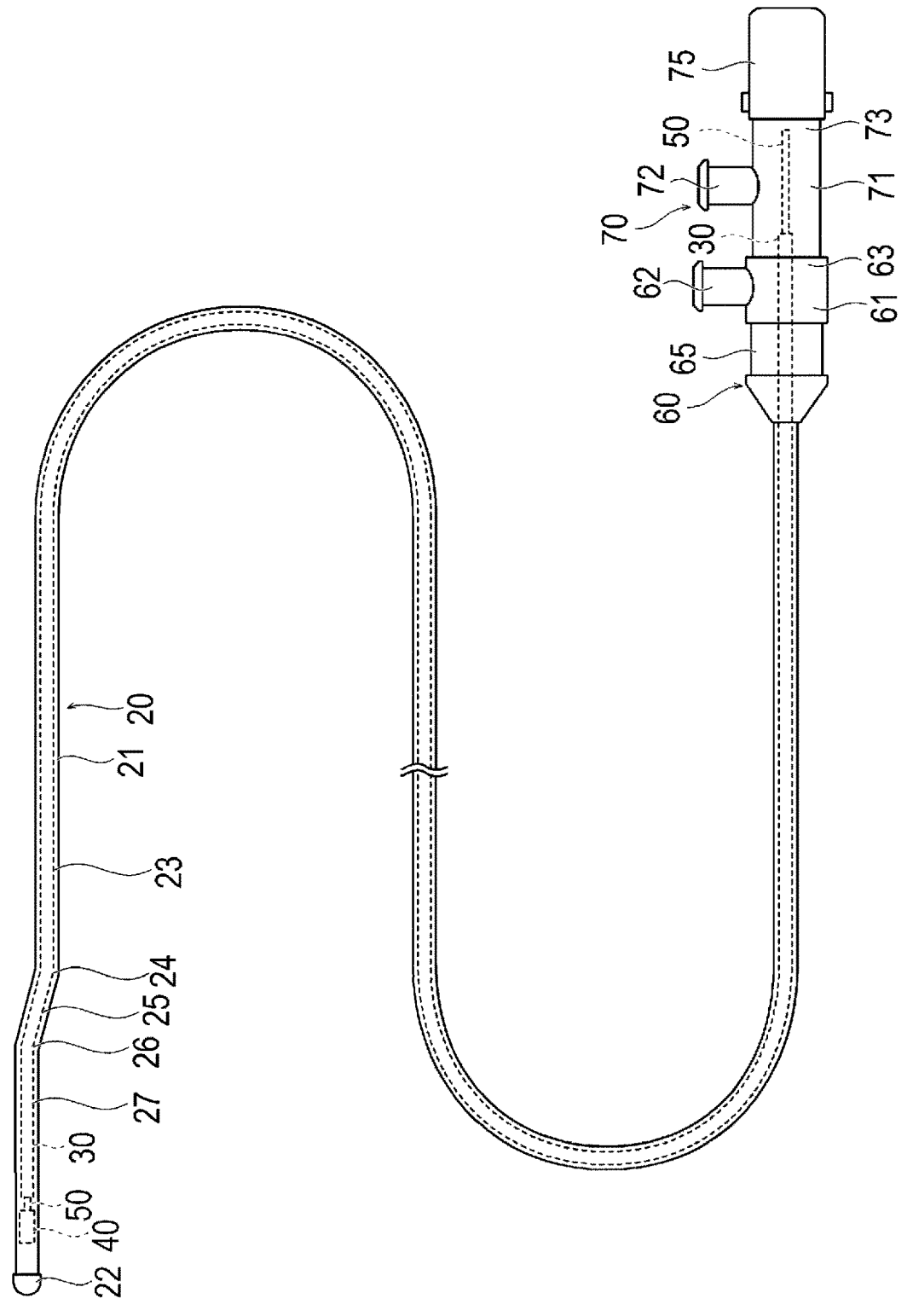
FIG. 1 is a plan view showing an ultrasound catheter according to an embodiment.

Set forth below with reference to the accompanying drawings is a detailed description of embodiments of an ultrasound catheter and an ultrasound catheter system that acquire an image by being inserted into an inner lumen such as a heart or a blood vessel. Note that since embodiments described below are preferred specific examples of the present disclosure, although various technically preferable limitations are given, the scope of the present disclosure is not limited to the embodiments unless otherwise specified in the following descriptions. Dimensional ratios in the drawings may be exaggerated and different from actual ratios for convenience of description. Further, in the present specification, a side to be inserted into a living body is referred to as a "distal side", and a side to be operated is referred to as a "proximal side".

An ultrasound catheter 10 according to the present embodiment is a device that can acquire a three-dimensional image of a heart or a blood vessel by being mainly inserted into the heart or the blood vessel.

Figures 2A, 2B:
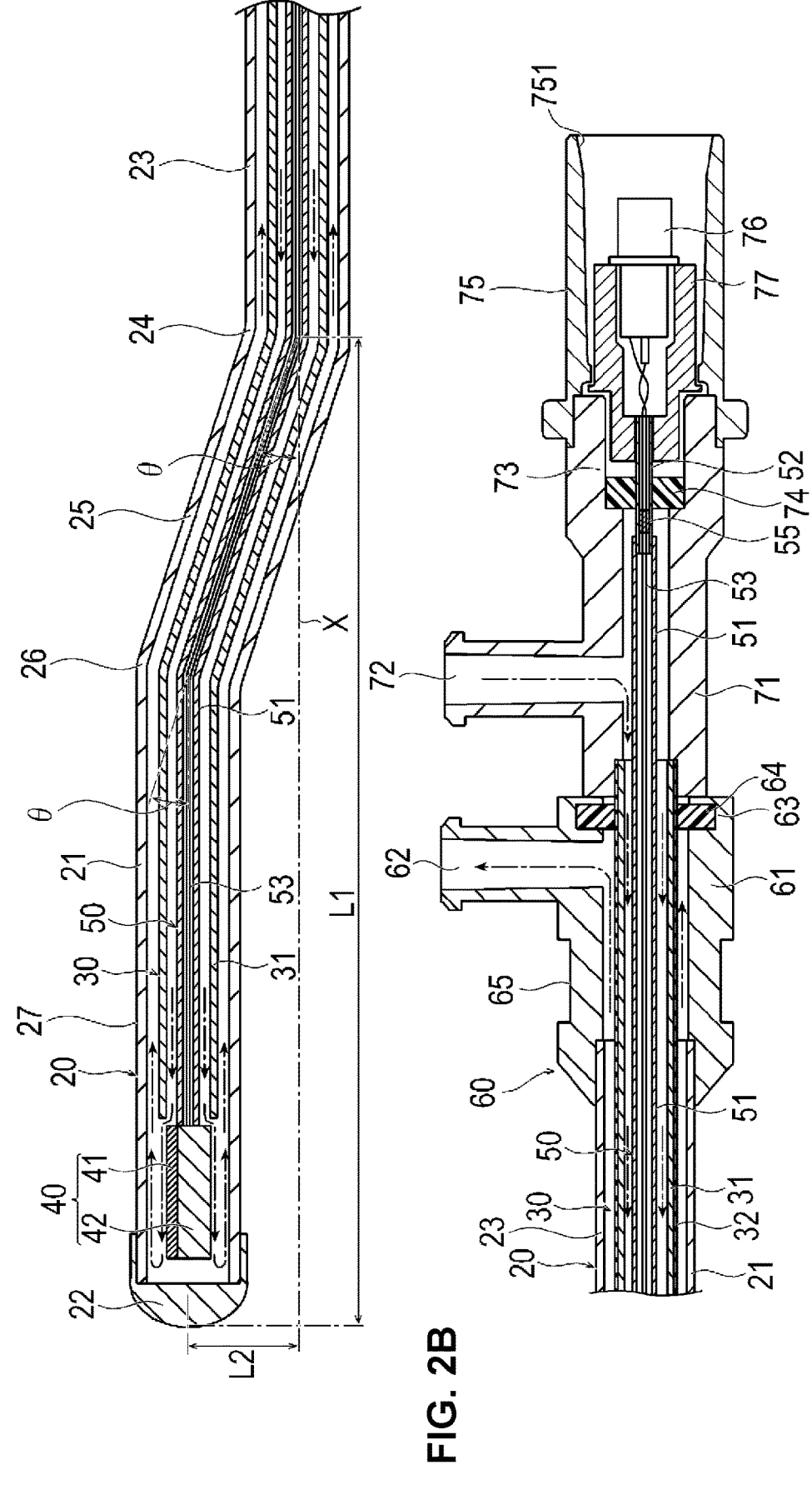

As shown in FIGS. 1 and 2, the ultrasound catheter 10 can include an outer sheath 20, an inner sheath 30, a transducer unit 40, and a drive shaft 50. The ultrasound catheter 10 further can include a first housing 60 and a second housing 70.

The outer sheath 20 is a tubular body to be inserted into an inner lumen of a living body. The outer sheath 20 includes an outer sheath body 21 and a distal end cap 22.

The outer sheath body 21 can include, from a proximal end toward a distal end, a proximal side tubular portion 23, a first bent portion 24 (bent portion), a first tubular portion 25 (tubular portion), a second bent portion 26 (bent portion), and a second tubular portion 27 (tubular portion). An accommodation lumen 28 that extends from the proximal end to the distal end of the outer sheath body 21 is formed inside the proximal side tubular portion 23, the first bent portion 24, the first tubular portion 25, the second bent portion 26, and the second tubular portion 27.

The proximal side tubular portion 23 is a tubular body having a substantially straight line-shaped axis. A proximal portion of the proximal side tubular portion 23 is fixed to the first housing 60. The first bent portion 24 is a tubular body positioned on a distal side of the proximal side tubular portion 23 and having a bent axis. The first tubular portion 25 is a tubular body positioned on a distal side of the first bent portion 24 and having a straight line-shaped axis. The second bent portion 26 is a tubular body positioned on a distal side of the first tubular portion 25 and having a bent axis. The second tubular portion 27 is a tubular body positioned on a distal side of the second bent portion 26 and having a straight line-shaped axis. A distal portion of the second tubular portion 27 is fixed to the distal end cap 22.

The axis of the proximal side tubular portion 23 may not be straight line-shaped, but may be curved to some extent. In this case, a radius of curvature of the axis of the first tubular portion 25 is larger than a radius of curvature of the axis of the first bent portion 24 and a radius of curvature of the second bent portion 26. That is, the proximal side tubular portion 23 has a shape closer to a straight line than the first bent portion 24 and the second bent portion 26. The straight line can be defined as having an infinite radius of curvature. The axis of at least a distal portion of the proximal side tubular portion 23 is positioned on a linear reference line X.

The axis of the first tubular portion 25 may not be straight line-shaped, but may be curved to some extent. In this case, a radius of curvature of the axis of the first tubular portion 25 is larger than the radius of curvature of the axis of the first bent portion 24 and the radius of curvature of the second bent portion 26. That is, the first tubular portion 25 has a shape closer to a straight line than the first bent portion 24 and the second bent portion 26.

The axis of the second tubular portion 27 may not be straight line-shaped, but may be curved to some extent. In this case, a radius of curvature of the axis of the second tubular portion 27 is larger than the radius of curvature of the axis of the first bent portion 24 and the radius of curvature of the second bent portion 26. That is, the second tubular portion 27 has a shape closer to a straight line than the first bent portion 24 and the second bent portion 26. The axis of the second tubular portion 27 is substantially parallel to the axis of the proximal side tubular portion 23, but may not be parallel to the axis of the proximal side tubular portion 23.

A bending angle θ of the first bent portion 24 and the second bent portion 26 is not particularly limited, but is preferably, for example, 5° to 20°. When the bending angle θ is too small, an offset amount L2 of a distal portion of the outer sheath 20 with respect to a proximal portion of the outer sheath 20 becomes relatively small. The offset amount L2 is a length from the reference line X to an axis of a portion farthest from the reference line X in a direction perpendicular to the reference line X among portions on the distal side of the first bent portion 24 of the outer sheath 20. When the bending angle θ of the first bent portion 24 or the second bent portion 26 is too large, rotation and movement in an axial direction of the drive shaft 50, which moves in the axial direction while rotating in a state of being bent inside the first bent portion 24 and the second bent portion 26, are likely to be hindered. On the contrary, when the bending angle θ of the first bent portion 24 and the second bent portion 26 has an appropriate size, it is relatively easy to set the offset amount L2 of the outer sheath 20 to a desirable value while stably maintaining the rotation and the movement in the axial direction of the drive shaft 50.

A distal portion length L1, which is a length along the reference line X from the first bent portion 24 to a most distal end of the outer sheath 20, is not particularly limited, but is preferably, for example, 20 mm to 150 mm. Therefore, a length along the reference line X of an offset portion (a portion where the axis deviates from the reference line X in a direction perpendicular to the reference line X) on the distal side of the first bent portion 24 of the outer sheath 20 can be appropriately set for use in the heart or the blood vessel having a large inner lumen. Further, when the distal portion length L1 is too short, the offset amount L2 of the distal portion of the outer sheath 20 with respect to the proximal portion of the outer sheath 20 is likely to be relatively small. When the distal portion length L1 is too long, the offset amount L2 of the distal portion of the outer sheath 20 with respect to the proximal portion of the outer sheath 20 is likely to be relatively large. On the contrary, when the distal portion length L1 is an appropriate length, it is relatively easy to set the offset amount L2 of the outer sheath 20 to a desirable value.

The offset amount L2 is not particularly limited, but is preferably, for example, 5 mm to 30 mm. When the offset amount L2 has an appropriate magnitude, it is relatively easy to bring the outer sheath 20 close to an observation target portion in the heart or the blood vessel having the large inner lumen.

The outer sheath body 21 accommodates the transducer unit 40, the inner sheath 30, and the drive shaft 50 in the accommodation lumen 28. The transducer unit 40, the inner sheath 30, and the drive shaft 50 in the outer sheath body 21 can move in the accommodation lumen 28 along the axis of the outer sheath body 21. Further, the transducer unit 40 and the drive shaft 50 in the outer sheath body 21 can rotate in the outer sheath body 21. The outer sheath body 21 is a cylindrical body that is open only at a proximal end and closed at a distal end by the distal end cap 22. The proximal portion of the proximal side tubular portion 23 that forms a proximal portion of the outer sheath body 21 is fixed to the first housing 60. The distal portion of the second tubular portion 27 that forms a distal portion of the outer sheath body 21 is fixed to the distal end cap 22. The proximal portion of the outer sheath body 21 may be provided with a reinforcing body such as a braided wire.

In the present embodiment, two bent portions are provided, but one bent portion may be provided, or three or more bent portions may be provided. Further, in the present embodiment, two tubular portions are provided, but one tubular portion may be provided, or three or more tubular portions may be provided.

The distal end cap 22 is a flexible member that closes an opening of the outer sheath body 21 on the distal side. Instead of the distal end cap 22, a member where a guide wire lumen is formed may be fixed to the distal portion of the outer sheath body 21. In this case, the ultrasound catheter 10 can be of a rapid exchange type having the guide wire lumen at the distal portion.

The inner sheath 30 is a cylindrical body where a part of the distal side is inserted into the outer sheath 20. The inner sheath 30 can include an inner sheath body 31 and an inner sheath reinforcing body 32. A distal portion of the inner sheath 30 is accommodated in the outer sheath body 21 so as to be movable along the axis of the outer sheath body 21. A proximal portion of the inner sheath 30 extends from the outer sheath body 21 and the first housing 60 to the proximal side, and is fixed to the second housing 70.

The inner sheath body 31 rotatably accommodates the drive shaft 50. A distal portion of the inner sheath body 31 is positioned relatively close to the transducer unit 40 on a proximal side of the transducer unit 40. The inner sheath reinforcing body 32 can be a circular tube that reinforces an outer peripheral surface of a proximal portion of the inner sheath body 31. The inner sheath reinforcing body 32 is provided in a predetermined range in which the inner sheath reinforcing body 32 is more likely to be exposed to the proximal side than the first housing 60. Therefore, the inner sheath 30 can stably reciprocate along the axis of the outer sheath 20 with respect to the outer sheath 20. Therefore, the inner sheath 30 can be satisfactorily pushed into the first housing 60. The inner sheath reinforcing body 32 may not be the circular tube. The inner sheath reinforcing body 32 may be, for example, a braided wire embedded in the inner sheath body 31.

When the large transducer unit 40 having a long ultrasound penetration depth is applied such that an image can be acquired in a relatively large space such as an inside of the heart or an inside of a blood vessel of a lower limb or an abdomen, an inner diameter of the outer sheath body 21 increases accordingly. Accordingly, increasing an outer diameter of the drive shaft 50 is not desirable because a load on a proximal portion of the drive shaft 50, a required rotational driving force, and a heat generation amount increase. However, when the outer diameter of the drive shaft 50 is excessively smaller than that of the transducer unit 40, a large space is generated between an inner peripheral surface of the outer sheath body 21 and an outer peripheral surface of the drive shaft 50. This large space between the inner peripheral surface of the outer sheath body 21 and the outer peripheral surface of the drive shaft 50 can cause unstable movement of the drive shaft 50 in the rotational direction and the axial direction. The inner sheath 30 is disposed in this large space, and stabilizes the movement of the drive shaft 50 in the rotational direction and the axial direction. The inner sheath 30 does not rotate together with the drive shaft 50. Therefore, the rotational driving force required for the drive shaft 50 and the heat generation amount do not increase.

The transducer unit 40 transmits and receives ultrasound to and from a lumen tissue. The transducer unit 40 can include a transducer 41 that transmits and receives the ultrasound, and a transducer holding portion 42 where the transducer 41 is disposed and which is fixed to the drive shaft 50. A maximum outer diameter of the transducer unit 40 in a cross section orthogonal to the axis of the drive shaft 50 is larger than a maximum outer diameter of a distal side drive shaft 51. The maximum outer diameter of the transducer unit 40 is about the same as a maximum outer diameter of the inner sheath 30, but is not limited to the maximum outer diameter of the transducer unit 40 being about the same as the maximum outer diameter of the inner sheath 30. The transducer unit 40 can move in the accommodation lumen 28 of the outer sheath body 21 in the axial direction of the outer sheath body 21 beyond the first bent portion 24 and the second bent portion 26. That is, the transducer unit 40 can move in the accommodation lumen 28 from the proximal side tubular portion 23 to the second tubular portion 27. Further, the transducer unit 40 can rotate around the axis in the accommodation lumen 28.

The materials that constituent the outer sheath body 21, the distal end cap 22, and the inner sheath body 31 are not particularly limited as long as the materials are flexible and have strength to some extent. For example, polyolefins such as polyethylene and polypropylene, polyamide, polyesters such as polyethylene terephthalate, fluorine-based polymers such as polytetrafluoroethylene (PTFE) and an ethylene-tetrafluoroethylene copolymer (ETFE), polyether ether ketone (PEEK), polyimide, and the like can be suitably used as the materials for the outer sheath body 21, the distal end cap 22, and the inner sheath body 31.

The material that constituents the inner sheath reinforcing body 32 is not particularly limited, and for example, stainless steel, polyimide, polyether ether ketone, or the like can be suitably used.

The drive shaft 50 transmits a rotational force and a moving force in the axial direction, which are applied from a drive device 80 (see FIG. 3), to the transducer unit 40. The drive shaft 50 includes the flexible distal side drive shaft 51 that passes through the inner sheath 30, and a connection pipe 52 fixed to a proximal portion of the distal side drive shaft 51. A distal end of the distal side drive shaft 51 is fixed to the transducer holding portion 42. The distal side drive shaft 51 can include, for example, a multilayer coil-shaped tubular body such as a three-layer coil whose winding direction is set to right, left, and right directions alternately. The connection pipe 52 can be, for example, a metal-made circular tube. A proximal portion of the connection pipe 52 is fixed to a rotor 77 that is rotated in the second housing 70. A signal line 53 passes through an inside of the connection pipe 52. The signal line 53 in the connection pipe 52 is adhered by a sealing agent 55 such as an adhesive. Therefore, a fluid cannot flow through the inside of the connection pipe 52.

When the drive shaft 50 transmits power of rotation, the transducer unit 40 is rotated, and an internal structure of a tissue can be observed 360 degrees from the blood vessel or a heart chamber. Further, the drive shaft 50 can move in the accommodation lumen 28 of the outer sheath body 21 along the axis of the outer sheath body 21.

The signal line 53 is disposed so as to pass through an inside of the drive shaft 50. The signal line 53 transmits a signal transmitted from the rotor 77 to the transducer unit 40. Further, the signal line 53 transmits a signal detected by the transducer unit 40 to the drive device 80 via the rotor 77.

In the first housing 60, the proximal portion of the outer sheath 20 is adhered in a liquid-tight manner. The first housing 60 includes a first hollow portion 61 that communicates with an inner lumen of the outer sheath 20, a first port 62, a first housing proximal portion 63, a first sealing portion 64, and an engagement portion 65.

The first hollow portion 61 communicates with the first port 62 and the accommodation lumen 28 of the outer sheath 20. The inner sheath 30 and the drive shaft 50, which extend from the outer sheath 20 toward the proximal side, pass through the first hollow portion 61. The first housing proximal portion 63 includes a through hole that communicates with the first hollow portion 61, and is positioned on the proximal side of the first hollow portion 61. The first sealing portion 64 is disposed in the through hole of the first housing proximal portion 63. The inner sheath 30 and the drive shaft 50 pass through the first sealing portion 64. The first sealing portion 64 is in relatively close contact with the first housing proximal portion 63 in a liquid-tight manner. The first sealing portion 64 is in contact with an outer peripheral surface of the inner sheath 30 so as to be slidable and rotatable along the axis of the inner sheath 30. The first sealing portion 64 is not particularly limited as long as it is slidable on the outer peripheral surface of the inner sheath 30, and can be, for example, an O-ring or a cross-cut valve body. The cross-cut valve body is a valve body in which a cut in one surface of a flexible material and a cut in the other surface are made to intersect with each other, and two cuts are made to communicate with each other at a central portion. The first port 62 is an opening portion to which a tube or the like for injecting or discharging a fluid such as a saline solution can be coupled.

The engagement portion 65 is a portion rotatably supported by a holding portion of the drive device 80 described later. The engagement portion 65 has a cylindrical shape and includes a smooth outer peripheral surface. The engagement portion 65 can be formed, for example, in a groove shape in an outer peripheral surface of the first housing 60.

The second housing 70 is disposed on a proximal side of the first housing 60. In the second housing 70, the proximal portion of the inner sheath 30 extends from the first housing 60 toward the proximal side and is adhered in a liquid-tight manner. The second housing 70 can move close to and away from the first housing 60 along the axis of the inner sheath 30.

The second housing 70 includes a second hollow portion 71 that communicates with an inner lumen of the inner sheath 30, a second port 72, a second housing proximal portion 73, and a second sealing portion 74. The second housing 70 further includes a joint 75, a connector 76, and the rotor 77.

The second hollow portion 71 allows the second port 72 and the inner lumen of the inner sheath 30 to communicate with each other. The drive shaft 50 extends from the inner sheath 30 toward the proximal side and passes through the second hollow portion 71. The second housing proximal portion 73 includes a through hole that communicates with the second hollow portion 71, and is positioned on a proximal side of the second hollow portion 71. The second sealing portion 74 is disposed in the through hole of the second housing proximal portion 73. The connection pipe 52 of the drive shaft 50 passes through the second sealing portion 74. The second sealing portion 74 is in contact with an outer peripheral surface of the connection pipe 52 so as to be slidable in a rotation direction of the connection pipe 52. The second sealing portion 74 slidably seals a space between the second housing proximal portion 73 and the drive shaft 50. The second sealing portion 74 is not particularly limited as long as it is slidable on the outer peripheral surface of the drive shaft 50, and can be, for example, an O-ring. The second port 72 is an opening portion to which a tube or the like for injecting or discharging a fluid such as a saline solution (saline) can be coupled.

The joint 75 is fixed to a proximal side of the second housing proximal portion 73. The joint 75 includes a joint opening portion 751 on the proximal side, and the connector 76 and the rotor 77 are disposed in the joint 75. The connector 76 can be coupled to a drive-side connector 811 of the drive device 80 (see FIG. 3) inserted through the joint opening portion 751. The connector 76 can be mechanically and electrically coupled to the drive-side connector 811. The signal line 53 that passes through an inside of the connection pipe 52 is connected to the connector 76. Therefore, the connector 76 is connected to the transducer unit 40 via the signal line 53.

The connection pipe 52 is adhered to the rotor 77. The rotor 77 is rotated integrally with the connector 76 in the joint 75. When the rotor 77 is rotated, the drive shaft 50 fixed to the rotor 77 is rotated. Further, the rotor 77 is sandwiched between the joint 75 and the second housing proximal portion 73, and movement of the rotor 77 in the axial direction can be limited. The rotor 77 can be rotated in the second housing 70, and can move along the axis together with the second housing 70. The transducer unit 40 outputs ultrasound in response to a signal received via the connector 76 and the signal line 53. Further, the transducer unit 40 receives a reflected wave, converts the reflected wave into a signal, and transmits the signal to the drive device 80 via the signal line 53 and the connector 76. The drive device 80 performs an appropriate processing on the received signal and displays the processed signal as an image.

The material that constituent the first housing 60 and the second housing 70 is not particularly limited as long as it has a strength to some extent. For example, polycarbonate, polyamide, polysulfone, polyarylate, a methacrylate-butylene-styrene copolymer, or the like can be suitably used as the material for the first housing 60 and the second housing 70.

Figure 3:
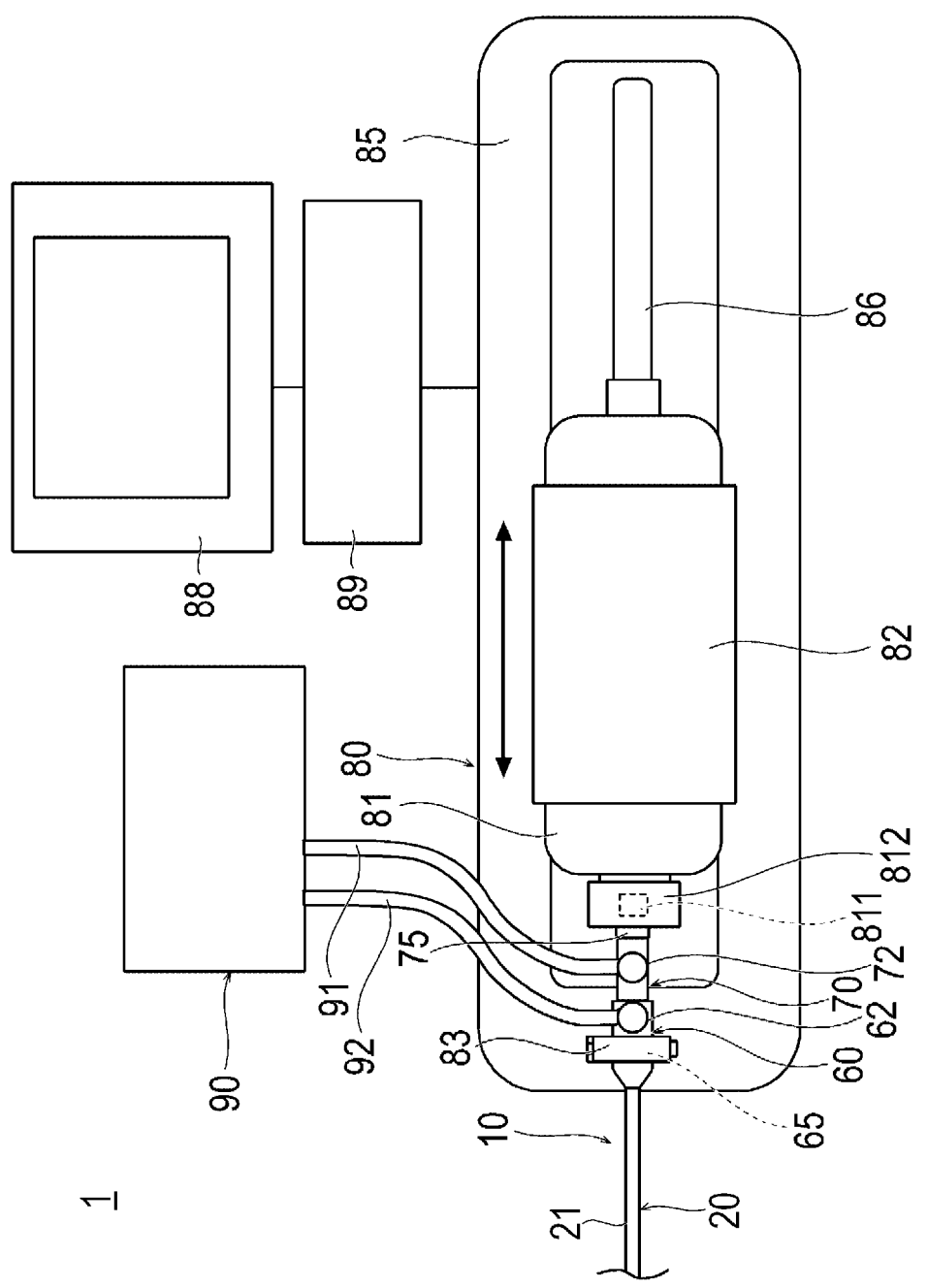
FIG. 3 is a schematic diagram showing an ultrasound catheter system including the ultrasound catheter.

As shown in FIGS. 3, 4A, and 4B, the ultrasound catheter 10 described above is connected to and driven by the drive device 80. The drive device 80 can include, on a base 85, a drive unit 81 that incorporates a drive source such as a motor and rotationally drives the drive shaft 50, a movement portion 82 that moves the drive unit 81 in an axial direction, and a distal side support portion 83 that rotatably supports the engagement portion 65 of the ultrasound catheter 10. The drive device 80 is connected to a control unit 89 that controls the drive unit 81 and the movement portion 82. An image obtained by the transducer unit 40 is displayed on a display unit 88 connected to the control unit 89.

The movement portion 82 can firmly hold the drive unit 81. The movement portion 82 can be, for example, a feed mechanism driven by a drive source such as a motor. The movement portion 82 moves the fixed drive unit 81 forward and backward along a groove rail 86 on the base 85.

The drive unit 81 includes a drive connector 811 that can be connected to the connector 76 of the ultrasound catheter 10, and a proximal side support portion 812 that can be connected to the joint 75 of the ultrasound catheter 10. When the connector 76 is connected to the drive connector 811, the drive unit 81 can transmit and receive a signal to and from the transducer unit 40, and can rotate the drive shaft 50.

The distal side support portion 83 can include a support base 93 that protrudes from the base 85, an outer ring 94 fixed to the support base 93, and an inner ring 95 slidably disposed inside the outer ring 94. The outer ring 94 can include two semi-circular arc-shaped outer ring members 96 that are divided so as to receive the engagement portion 65 of the ultrasound catheter 10 from an outside, a hinge portion 97 that couples the two outer ring members 96 in an openable and closable manner, and a fixing mechanism 98 that can fix the two outer ring members 96 in a closed state and can release the fixing. The fixing mechanism 98 can include, for example, a hook and a portion with which the hook is detachably engaged, but the structure is not limited to a hook and a portion with which the hook is detachably engaged. The inner ring 95 can include two semi-circular arc-shaped inner ring members 99 that are divided so as to receive the engagement portion 65 of the ultrasound catheter 10 from an outside. The inner ring members 99 surround and are in relatively close contact with the engagement portion 65, and can be rotated together with the engagement portion 65 in the outer ring 94. That is, the outer ring 94 and the inner ring 95 constitute a bearing. The structure of the distal side support portion is not particularly limited as long as the engagement portion 65 of the ultrasound catheter 10 can be rotatably supported.

Ultrasound scanning of the ultrasound catheter 10 is performed by transmitting a rotational motion of the drive unit 81 to the drive shaft 50 and rotating the transducer unit 40 fixed to a distal end of the drive shaft 50. Accordingly, ultrasound transmitted and received by the transducer 41 can be used to scan in a substantially radial direction. Further, the movement portion 52 can pull the drive shaft 50 toward the proximal side. Accordingly, the transducer 41 can be moved toward the proximal side while being rotated. Therefore, a 360° cross-sectional image of a surrounding tissue of the blood vessel or the heart chamber can be obtained in a scanning manner along the axis of the outer sheath 20 to any position.

The ultrasound catheter 10 is connected to a pump device 90. The pump device 90 can circulate a fluid. The pump device 90 can include a supply pipe 91 that supplies the fluid and a recovery pipe 92 that recovers the fluid. The supply pipe 91 is connected to the second port 72. The recovery pipe 92 is connected to the first port 62. A pump mechanism of the pump device 90 is not particularly limited, and can be, for example, a peristaltic pump, a centrifugal pump, a diaphragm pump, or the like. The pump device 90 may be of a non-circulation type. In this case, the first port 62 is connected to a tube connected to a waste container.

The ultrasound catheter 10, the drive device 80, the display unit 88, the control unit 89, and the pump device 90 constitute one ultrasound catheter system 1.

Figure 7:
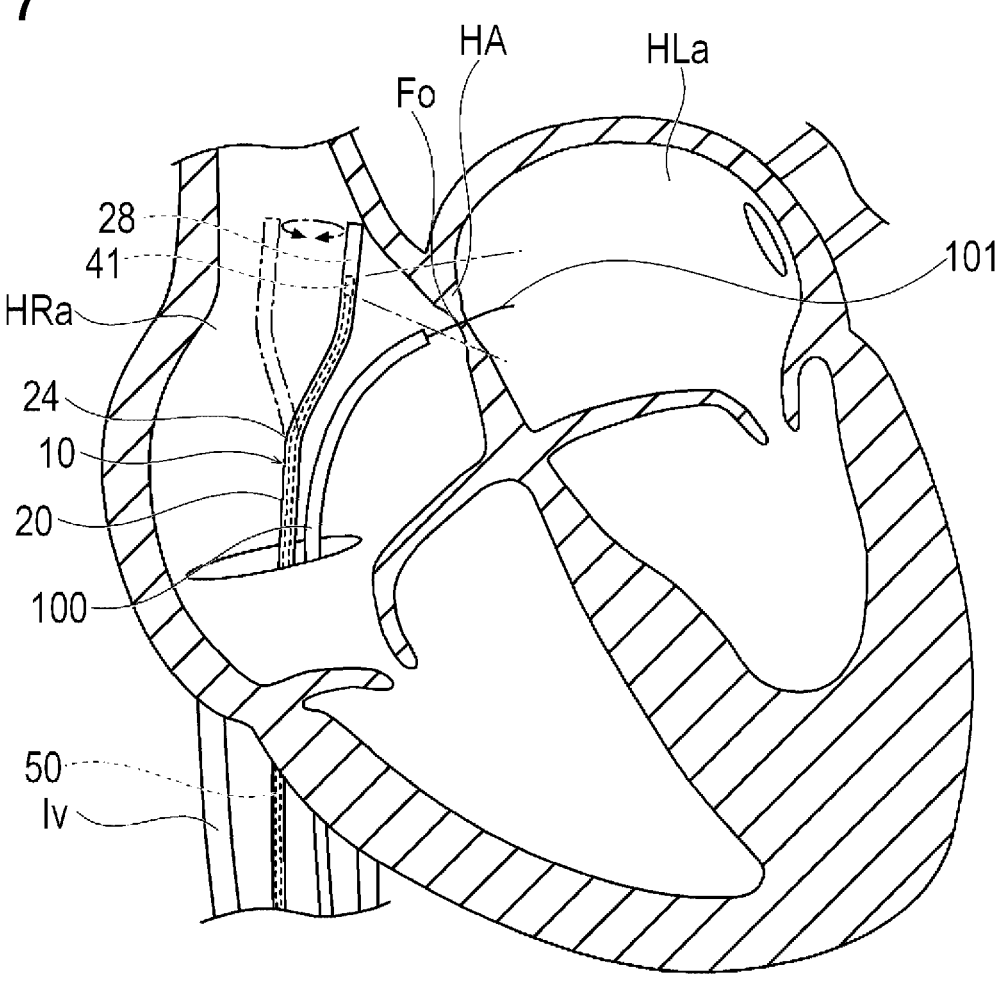
FIG. 7 is an illustrative view of a treatment method using the ultrasound catheter according to the present embodiment, in which the ultrasound catheter uses a front view, a biotissue uses a cross-sectional view, and both the front view and the cross-sectional view are illustrative views schematically showing the ultrasound catheter and the biotissue, respectively.

Next, a method for observing a biotissue from a lumen in a living body by using the ultrasound catheter 10 according to the present embodiment will be described. Here, as shown in FIG. 7, a treatment in which the ultrasound catheter 10 is inserted into a right atrium HRa from a femoral vein and an atrial septum HA is punctured will be described as an example.

First, before the ultrasound catheter 10 is inserted into the blood vessel, as shown in FIG. 3, the supply pipe 91 of the pump device 90 is connected to the second port 72, and the recovery pipe 92 is connected to the first port 62.

Next, as shown in FIGS. 2 and 3, the second housing 70 is brought closest to the first housing 60. At this time, the transducer unit 40 is positioned in the vicinity of a distal end of the outer sheath body 21. Since the inner sheath 30 covers the drive shaft 50 over substantially an entire length, the drive shaft 50 stably rotates during driving, and it is possible to receive a signal and acquire an image with relatively high accuracy.

Next, the pump device 90 is driven to inject, for example, the saline solution into the second hollow portion 71 from the second port 72 of the second housing 70. Accordingly, the saline solution flows into a gap between the drive shaft 50 and the inner sheath 30, as indicated by an alternate long and short dash line in FIGS. 2A and 2B. The drive shaft 50 rotatably passes through the second housing 70. However, a space between the second housing 70 and the drive shaft 50 is sealed by the second sealing portion 74. Therefore, the saline solution does not leak to an outside from the space between the second housing 70 and the drive shaft 50. Therefore, the saline solution can be effectively introduced into the inner sheath 30. The saline solution injected into the gap between the inner sheath 30 and the drive shaft 50 moves toward the distal side and reaches the distal side with respect to the inner sheath 30. Accordingly, a space between the outer sheath 20 and the transducer unit 40 is filled with the saline solution. The distal portion of the outer sheath body 21 is closed without forming an opening. Therefore, the saline solution is not discharged from the distal portion of the outer sheath body 21.

Next, the saline solution flows into a gap between the outer sheath 20 and the inner sheath 30 from a distal side of the inner sheath 30, and the saline solution moves to the proximal side in the gap. Thereafter, the saline solution flows into the first hollow portion 61 of the first housing 60. The inner sheath 30 passes through the first housing 60 so as to be movable along the axis. However, a space between the first housing 60 and the inner sheath 30 is sealed by the first sealing portion 64. Therefore, the saline solution does not leak to an outside from the space between the first housing 60 and the inner sheath 30. Therefore, the saline solution can be effectively discharged from the first port 62. Accordingly, air in the ultrasound catheter 10 can be removed, and a periphery of the transducer unit 40 can be filled with the saline solution.

Next, circulation of the saline solution is continued or stopped by the pump device 90, and the ultrasound catheter 10 can be inserted into the lumen in the living body.

Next, a surgeon percutaneously inserts the ultrasound catheter 10 into the femoral vein. Then, as shown in FIG. 7, under observation with X-rays, the surgeon pushes forward the ultrasound catheter 10 inserted into the blood vessel, and causes the ultrasound catheter 10 to reach the right atrium HRa via an inferior vena cava Iv. The surgeon disposes a most distal end of the ultrasound catheter 10 at a position beyond an oval fossa Fo that is an observation target (on a side close to a superior vena cava with respect to the oval fossa Fo). Further, the surgeon percutaneously inserts a sheath 100 into the femoral vein, and causes the sheath 100 to reach the right atrium HRa via the inferior vena cava Iv.

Thereafter, as shown in FIGS. 3 and 5, the ultrasound catheter 10 is coupled to the drive device 80. That is, the engagement portion 65 of the first housing 60 is surrounded by the two inner ring members 99, and the engagement portion 65 and the inner ring members 99 are disposed between the two outer ring members 96 in an open state. Thereafter, the two outer ring members 96 are closed, and fixed by the fixing mechanism 98. Accordingly, the first housing 60 is supported by the distal side support portion 83 so as to be rotatable and immovable in the axial direction.

Next, the joint 75 of the ultrasound catheter 10 is connected to the proximal side support portion 812 of the drive unit 81. Accordingly, a signal can be transmitted and received between the transducer unit 40 and the drive device 80. Further, the drive shaft 50 can rotate and move by the drive unit 81 and the movement portion 82.

Figures 6A, 6B:
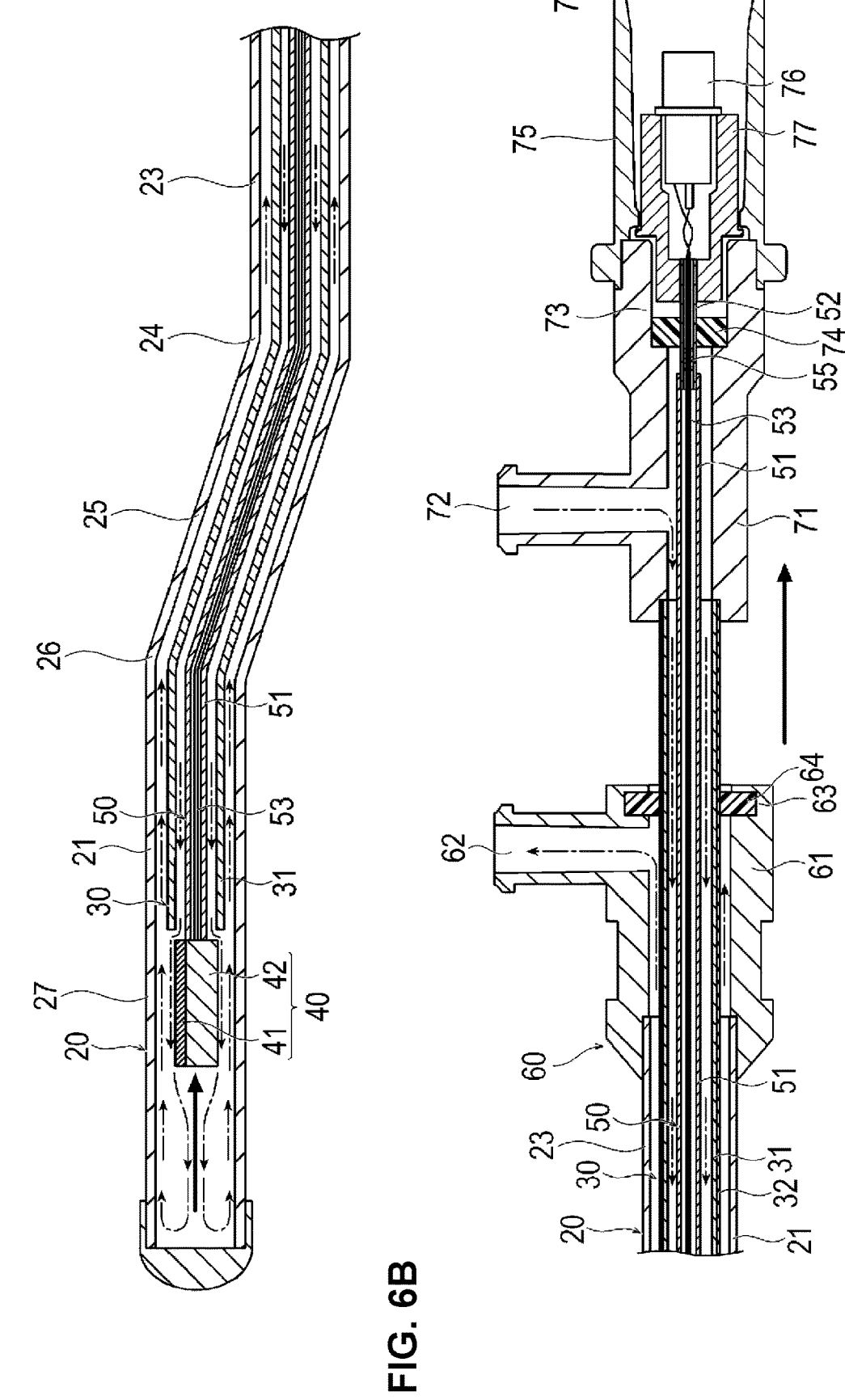

Next, as shown in FIGS. 6A and 6B, the surgeon performs a pull-back operation while rotating the drive shaft 50 while acquiring image data from the transducer unit 40 by the drive device 80. The pull-back operation can be performed by operating the movement portion 82 connected to the proximal portion of the ultrasound catheter 10 by the control unit 89. The acquired data is subjected to a digital processing by the control unit 89, and then displayed on the display unit 88 as image data (see FIG. 3). The display unit 88 can display the image data substantially in real time. The surgeon disposes the transducer 41 at a specific position in a rotation direction and an axial direction in which the oval fossa Fo can be observed while checking the display unit 88.

Next, the surgeon rotates the first housing 60 rotatably supported by the distal side support portion 83 to rotate the outer sheath 20 in a state where pull-back and rotation of the drive shaft 50 by the drive device 80 are fixed. The outer sheath 20 includes the first bent portion 24 at the distal portion of the outer sheath 20. Therefore, the surgeon can freely adjust a distance and an angle of an offset portion of the outer sheath 20 on the distal side of the first bent portion 24 with respect to the observation target. When an offset lower portion of the outer sheath 20 is rotated, positions of the transducer 41 and the drive shaft 50 disposed in the accommodation lumen 28 also change accordingly. Therefore, the surgeon can freely adjust the distance and the angle of the transducer 41 disposed in the accommodation lumen 28 of the outer sheath 20 with respect to the observation target. For example, by rotating the outer sheath 20, the surgeon can bring the transducer 41 relatively close to the oval fossa Fo that is an observation target such that the oval fossa Fo can be rather easily observed.

Next, the surgeon causes a septum puncture needle 101 to reach the right atrium HRa via the sheath 100. Next, the surgeon checks that the septum puncture needle 101 is directed toward the oval fossa Fo under ultrasound observation by the ultrasound catheter 10. Thereafter, the surgeon punctures the oval fossa Fo with the septum puncture needle 101 under the ultrasound observation. Accordingly, it is possible to reliably prevent a portion other than the oval fossa Fo from being punctured by the septum puncture needle 101. Thereafter, the surgeon removes the septum puncture needle 101, the sheath 100, and the ultrasound catheter 10, and completes the procedure.

As described above, the ultrasound catheter 10 according to the present embodiment includes: the outer sheath 20 in which the accommodation lumen 28 that extends from the proximal end to the distal end is formed; the inner sheath 30 that can move in the accommodation lumen 28 along the axis of the outer sheath 20; the drive shaft 50 that can rotate in the inner sheath 30 and/or the outer sheath 20; and the transducer 41 that is disposed on the distal side of the inner sheath 30 in the accommodation lumen 28, and that is fixed to the distal end of the drive shaft 50, in which the outer sheath 20 includes the first bent portion 24 that is bent and shaped in advance at a predetermined angle on the proximal side of a most distal end of the accommodation lumen 28, and the first tubular portion 25 and the second tubular portion 27 that have the axis having the radius of curvature larger than the radius of curvature of the axis of the first bent portion 24, the first tubular portion 25 and the second tubular portion 27 being positioned on the distal side of the first bent portion 24 and on the proximal side of the most distal end of the accommodation lumen 28, in which the outer sheath 20 is rotatable with respect to the inner sheath 30.

Since the outer sheath 20 is rotated with respect to the inner sheath 30, the ultrasound catheter 10 configured as described above can freely adjust the distance and the angle of the transducer 41, which is in the accommodation lumen 28 positioned in the first tubular portion 25 and the second tubular portion 27 on the distal side of the first bent portion 24, with respect to the observation target. Therefore, the ultrasound catheter 10 can acquire an image of the observation target with relatively high accuracy even when the ultrasound catheter 10 is inserted into a large inner lumen.

The axes of the first tubular portion 25 and the second tubular portion 27 are linear. Accordingly, since the transducer 41 to be moved in the accommodation lumen 28 is moved linearly, obtained images can be rather easily connected in the axial direction, and a relatively highly accurate three-dimensional image can be acquired.

The outer sheath 20 can include the first bent portion 24 and the second bent portion 26 at different positions in the axial direction. Accordingly, as compared with a case where the outer sheath 20 includes only one bent portion, it is relatively easy to dispose the transducer 41 at a desirable position.

The second tubular portion 27, which is at least one of the bent portions, is bent toward a side opposite to the first tubular portion 25, which is at least one of other bent portions. Accordingly, the distal portion of the outer sheath 20 can be disposed at a position offset from the proximal portion of the outer sheath 20 while having a shape close to parallel to the proximal portion of the outer sheath 20. Therefore, the distal portion of the outer sheath 20 is rather easily disposed along a wall of the inner lumen of the heart or the inner lumen such as a blood vessel. Therefore, the transducer 41 that pulls back along the axis can be disposed at a desirable position with respect to the observation target in a large range of the outer sheath 20 in the axial direction.

The transducer 41 can move in the accommodation lumen 28 in the axial direction beyond the first bent portion 24 and the second bent portion 26. Accordingly, the transducer 41 can acquire an image of an internal structure of a living body positioned in a large range beyond the first bent portion 24 and the second bent portion 26 in an axial direction of the accommodation lumen 28.

The bending angle of the axis of the first bent portion 24 and the second bent portion 26 can be, for example, 5° to 20°. When the bending angle is not too small, it is relatively easy to set the offset amount L2 of the outer sheath 20 to a desirable value. Further, when the bending angle is not too large, rotation and movement in the axial direction of the drive shaft 50, which moves in the axial direction while being rotated in a state of being bent in the bent portion, are less likely to be hindered.

The outer sheath 20 includes the proximal side tubular portion 23 on the proximal side of the first bent portion 24 that is a bent portion on a most proximal side. The distal portion length L1, which is a length from the first bent portion 24 to the most distal end of the outer sheath 20 along the linear reference line X where the axis of at least the distal portion of the proximal side tubular portion 23 is positioned, is 20 mm to 150 mm. Accordingly, a length of a portion offset with respect to the proximal side tubular portion 23 can be set to a length appropriate for observation in a heart or a blood vessel having a large inner lumen. Further, since the distal portion length L1 is an appropriate length, it is rather easy to set the offset amount L2 of the outer sheath 20 to a length appropriate for observation in the heart or the blood vessel having the large inner lumen.

The outer sheath 20 includes the proximal side tubular portion 23 on the proximal side of the first bent portion 24 that is a bent portion on the most proximal side. The offset amount L2 that is a length from the linear reference line X where the axis of at least the distal portion of the proximal side tubular portion 23 is positioned to the axis of the portion farthest in the direction perpendicular to the reference line X of a portion on the distal side of the first bent portion 24 of the outer sheath 20 is 5 mm to 30 mm. Since the offset amount L2 has an appropriate magnitude, it is rather easy to bring the outer sheath 20 close to the observation target in the heart or the blood vessel having the large inner lumen.

The ultrasound catheter system 1 according to the present embodiment includes the ultrasound catheter 10 and the drive device 80 that drives the ultrasound catheter 10, in which the ultrasound catheter 10 includes the outer sheath 20 in which the accommodation lumen 28 that extends from the proximal end to the distal end is formed; the inner sheath 30 that can move in the accommodation lumen 28 along the axis of the outer sheath 20; the drive shaft 50 that can rotate in the inner sheath 30 and/or the outer sheath 20; the transducer 41 disposed on the distal side of the inner sheath 30 in the accommodation lumen 28, and fixed to the distal end of the drive shaft 50; the first housing 60 to which the proximal portion of the outer sheath 20 is fixed and through which the drive shaft 50 and the inner sheath 30 pass; and the second housing 70 that is disposed on the proximal side of the first housing 60, to which the proximal portion of the inner sheath 30 is fixed, and that rotatably holds the drive shaft 50, in which the outer sheath 20 includes the first bent portion 24 that is bent and shaped in advance at a predetermined angle on the proximal side of the most distal end of the accommodation lumen 28, and the first tubular portion 25 and the second tubular portion 27 that have the axis having the radius of curvature larger than the radius of curvature of the axis of the first bent portion 24, the first tubular portion 25 and the second tubular portion 27 being positioned on the distal side of the first bent portion 24 and on the proximal side of the most distal end of the accommodation lumen 28, in which the outer sheath 20 is rotatable with respect to the inner sheath 30, in which the drive device 80 includes the proximal side support portion 812 that can support the second housing 70, the movement portion 82 that can move the proximal side support portion 812 in the axial direction, the drive unit 81 that can transmit the rotational force to the drive shaft 50, and the distal side support portion 83 that can rotatably support the first housing 60.

Since the first housing 60 supported by the distal side support portion 83 is rotatable, by rotating the outer sheath 20 fixed to the first housing 60 with respect to the inner sheath 30, the ultrasound catheter system 1 configured as described above can freely adjust the distance and the angle of the transducer 41, which is in the accommodation lumen 28 positioned in the first tubular portion 25 and the second tubular portion 27 on the distal side of the first bent portion 24, with respect to the observation target. Therefore, the ultrasound catheter system 1 can acquire an image of the observation target with high accuracy even when the ultrasound catheter system 1 is inserted into, for example, a large inner lumen.

Further, the present disclosure also provides a treatment method. The present treatment method includes: inserting, into the blood vessel, the ultrasound catheter 10 in which the transducer 41 rotatable and movable in the axial direction is provided in the outer sheath 20 in which the accommodation lumen 28 that extends from the proximal end to the distal end is formed and that includes the bent portion bent and shaped in advance at a predetermined angle on the proximal side of the most distal end of the accommodation lumen 28, and causing the ultrasound catheter 10 to reach the right atrium HRa via the inferior vena cava Iv; acquiring an ultrasound image by moving the transducer 41 along the axis while rotating the transducer 41 in the accommodation lumen 28; rotating the outer sheath 20 to adjust a position of a portion on the distal side of the bent portion of the outer sheath 20 with respect to the oval fossa Fo that is an observation target; and acquiring an ultrasound image of the oval fossa Fo by the transducer 41.

In the treatment method configured as described above, by rotating the outer sheath 20 of the ultrasound catheter 10 inserted into the large inner lumen of the heart, the position and the angle of the transducer 41, which is disposed in the outer sheath 20 on the distal side of the bent portion of the outer sheath 20, with respect to the oval fossa Fo can be freely adjusted. Therefore, in the present treatment method, it is possible to acquire an image of the oval fossa Fo, which is the observation target, with relatively high accuracy even when the treatment is performed in the large inner lumen of the heart. Therefore, in the present treatment method, for example, it is possible to safely puncture the oval fossa Fo while checking the oval fossa Fo.

Figure 8:
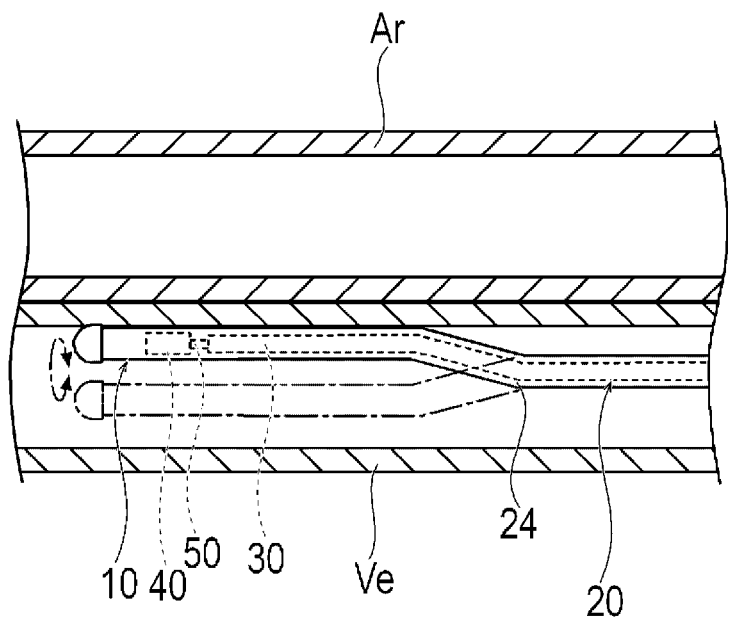
FIG. 8 is an illustrative view of another example of the treatment method using the ultrasound catheter according to the present embodiment, in which the ultrasound catheter uses a front view, the biotissue uses a cross-sectional view, and both the front view and the cross-sectional view are illustrative views schematically showing the ultrasound catheter and the biotissue, respectively.

The present disclosure is not limited to the embodiment described above, and various modifications can be made by those skilled in the art within a scope of the technical idea of the present disclosure. For example, as shown in FIG. 8, the ultrasound catheter 10 according to the present embodiment may be inserted into one of two adjacent blood vessels and used to observe a blood vessel into which the ultrasound catheter 10 is not inserted. For example, the ultrasound catheter 10 can be inserted into a vein Ve of a lower limb or an abdomen to observe an inside of an artery Ar adjacent to the vein Ve. Therefore, for example, when a procedure of inserting an atherectomy device into an artery and scraping and removing a calcified lesion is performed, the calcified lesion and the atherectomy device in the artery Ar can be observed.

Figures 9A, 9B, 9C:
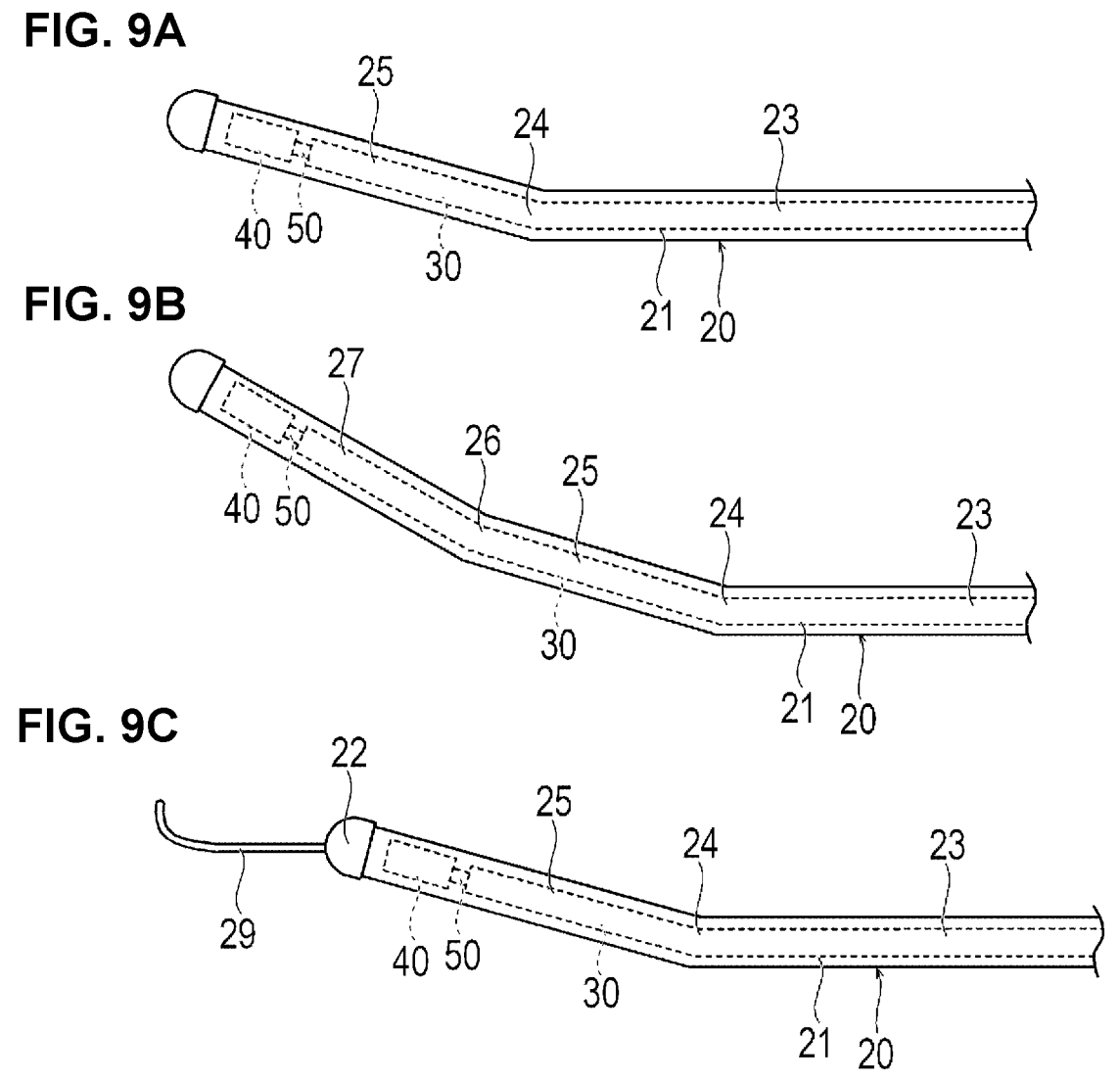

As in a first modification shown in FIG. 9A, only one bent portion (for example, the first bent portion 24) may be provided.

As in a second modification shown in FIG. 9B, the ultrasound catheter 10 may include at least two bent portions (for example, the first bent portion 24 and the second bent portion 26) bent toward the same side. Accordingly, in the outer sheath 20, respective angles of the first bent portion 24 and the second bent portion 26 can be reduced. Therefore, it is possible to reduce a load on the drive shaft 50 that is movable in an axial direction while being rotated in the first bent portion 24 and the second bent portion 26, and to help prevent occurrence of a rotation failure or a failure in movement in the axial direction. Further, since the outer sheath 20 can be largely bent as a whole by at least two bent portions, orientation is facilitated.

As in a third modification shown in FIG. 9C, in the ultrasound catheter 10, a wire 29 that protrudes from a distal end of the outer sheath 20 in a distal end direction may be formed. An outer diameter of the wire 29 is smaller than an outer diameter of the outer sheath 20. A distal portion of the wire 29 is curved. The wire 29 has a function as a guide wire for selecting a blood vessel to be advanced when the ultrasound catheter 10 is pushed forward in the blood vessel. Accordingly, the ultrasound catheter 10 is rather easily pushed forward in a blood vessel.

The detailed description above describes embodiments of an ultrasound catheter and an ultrasound catheter system that acquire an image by being inserted into an inner lumen such as a heart or a blood vessel. These disclosed embodiments represent examples of the ultrasound catheter and the ultrasound catheter system that acquire an image by being inserted into an inner lumen such as a heart or a blood vessel disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An ultrasound catheter comprising:

an outer sheath, the outer sheath includes an accommodation lumen configured to extend from a proximal end to a distal end of the outer sheath;

an inner sheath configured to move in the accommodation lumen along an axis of the outer sheath;

a drive shaft configured to rotate in the inner sheath and/or the outer sheath;

a transducer disposed on a distal side of the inner sheath in the accommodation lumen, and fixed to a distal end of the drive shaft;

the outer sheath includes a bent portion, the bent portion being bent and shaped in advance at a predetermined angle on a proximal side of a most distal end of the accommodation lumen, and a tubular portion having an axis having a radius of curvature larger than a radius of curvature of an axis of the bent portion, the tubular portion being positioned on a distal side of the bent portion and on the proximal side of the most distal end of the accommodation lumen;

wherein the outer sheath is configured to be rotatable with respect to the inner sheath;

wherein the axis of the outer sheath is bent at the bent portion so as to define a bent angle of the bent portion;

wherein the inner sheath extends to a vicinity of a proximal end of the transducer, so as to cover substantially an entire length of the drive shaft; and wherein both the drive shaft and the inner sheath are configured to be inserted into the tubular portion of the outer sheath beyond the bent portion such that the transducer moves in the accommodation lumen in an axial direction beyond the bent portion.

2. The ultrasound catheter according to claim 1, wherein the axis of the tubular portion is linear.

3. The ultrasound catheter according to claim 1, wherein the bent portion of the outer sheath includes two or more bent portions, the two or more bent portion being at different positions in an axial direction.

4. The ultrasound catheter according to claim 3, further comprising:

at least one of the two or more bent portions is bent toward a side opposite to at least one of another of the two or more bent portions.

5. The ultrasound catheter according to claim 3, further comprising:

at least two of the two or more bent portions are bent toward the same side.

6. The ultrasound catheter according to claim 1, wherein a bending angle of the axis of the bent portion is 5° to 20°.

7. The ultrasound catheter according to claim 1, wherein the outer sheath includes a proximal side tubular portion on a proximal side of a bent portion on a most proximal side; and the most distal end of the accommodation lumen is away from a linear reference line, in which the axis of the outer sheath at a distal portion of the proximal side tubular portion, in a direction perpendicular to the linear reference line.

8. The ultrasound catheter according to claim 7, wherein an offset amount, which is a length from the linear reference line to the axis of the tubular portion at a distal portion of the tubular portion in the direction perpendicular to the linear reference line, is 5 mm to 30 mm.

9. The ultrasound catheter according to claim 1, wherein the outer sheath includes a proximal side tubular portion disposed proximal of the bent portion;

wherein the bent portion of the outer sheath includes a first bent portion and a second bent portion, the first bent portion disposed distal of the proximal side tubular portion, the second bent portion disposed distal of the first bent portion and proximal of the tubular portion and bent toward a side opposite to the first bent portion; and wherein the axis of the outer sheath is bent at both the first bent portion and the second bent portion so as to define a bent angle of the first bent portion and the second bent portion.

10. An ultrasound catheter system comprising:

an ultrasound catheter;

a drive device configured to drive the ultrasound catheter;

the ultrasound catheter including:

an outer sheath in which an accommodation lumen configured to extend from a proximal end to a distal end of the outer sheath;

an inner sheath configured to move in the accommodation lumen along an axis of the outer sheath;

a drive shaft configured to rotate in the inner sheath and/or the outer sheath;

a transducer that is disposed on a distal side of the inner sheath in the accommodation lumen, and wherein the transducer is fixed to a distal end of the drive shaft;

a first housing to which a proximal portion of the outer sheath is fixed and through which the drive shaft and the inner sheath pass; and a second housing that is disposed on a proximal side of the first housing, to which a proximal portion of the inner sheath is fixed, and wherein the second house is configured to rotatably hold the drive shaft;

the outer sheath including:

a bent portion that is bent and shaped in advance at a predetermined angle on a proximal side of a most distal end of the accommodation lumen; and a tubular portion that has an axis having a radius of curvature larger than a radius of curvature of an axis of the bent portion, the tubular portion being positioned on a distal side of the bent portion and on the proximal side of the most distal end of the accommodation lumen;

the outer sheath configured to be rotatable with respect to the inner sheath;

the drive device includes a proximal side support portion configured to support the second housing, a movement portion configured to move the proximal side support portion in an axial direction, a drive unit configured to transmit a rotational force to the drive shaft, and a distal side support portion configured to rotatably support the first housing;

wherein the inner sheath extends to a vicinity of a proximal end of the transducer so as to cover substantially an entire length of the drive shaft; and wherein both the drive shaft and the inner sheath are configured to be inserted into the tubular portion of the outer sheath beyond the bent portion such that the transducer moves in the accommodation lumen in an axial direction beyond the bent portion.

11. The ultrasound catheter system according to claim 10, wherein the axis of the tubular portion is linear.

12. The ultrasound catheter system according to claim 10, wherein the bent portion of the outer sheath includes two or more bent portions, the two or more bent portion being at different positions in an axial direction.

13. The ultrasound catheter system according to claim 12, further comprising:

at least one of the two or more bent portions is bent toward a side opposite to at least one of another of the two or more bent portions.

14. The ultrasound catheter system according to claim 12, further comprising:

at least two of the two or more bent portions are bent toward the same side.

15. The ultrasound catheter system according to claim 10, wherein the outer sheath includes a proximal side tubular portion on a proximal side of a bent portion on a most proximal side; and a distal portion length, which is a length from the bent portion on a most proximal side to a most distal end of the outer sheath along a linear reference line where an axis of at least a distal portion of the proximal side tubular portion is positioned, is 20 mm to 150 mm.

16. The ultrasound catheter system according to claim 10, wherein the outer sheath includes the proximal side tubular portion on the proximal side of the bent portion on the most proximal side; and an offset amount, which is a length from the linear reference line where the axis of at least the distal portion of the proximal side tubular portion is positioned to an axis of a portion farthest in a direction perpendicular to the reference line of a portion on a distal side of the bent portion of the outer sheath on the most proximal side, is 5 mm to 30 mm.

17. The ultrasound catheter system according to claim 10, wherein the outer sheath includes a proximal side tubular portion disposed proximal of the bent portion; and wherein the bent portion of the outer sheath includes a first bent portion and a second bent portion, the first bent portion disposed distal of the proximal side tubular portion, the second bent portion disposed distal of the first bent portion and proximal of the tubular portion and bent toward a side opposite to the first bent portion; and wherein the axis of the outer sheath is bent at both the first bent portion and the second bent portion so as to define a bent angle of the first bent portion and the second bent portion.

18. An ultrasound catheter comprising:

an outer sheath, the outer sheath includes an accommodation lumen configured to extend from a proximal end to a distal end of the outer sheath;

a drive shaft configured to move in an axial direction of the outer sheath;

a transducer fixed to a distal end of the drive shaft;

wherein the outer sheath includes a proximal side tubular portion, a bent portion disposed distal of the proximal side tubular portion, and a tubular portion disposed distal of the bent portion, the bent portion being bent and shaped in advance at a predetermined angle, the tubular portion having a linear axis, the tubular portion being positioned on a distal side of the bent portion and on the proximal side of the most distal end of the accommodation lumen;

the outer sheath is rotatable with respect to the drive shaft;

wherein the transducer is configured to move in the accommodation lumen in the axial direction of the outer sheath beyond the bent portion;

wherein the axis of the outer sheath is bent at the bent portion so as to define a bent angle of the bent portion; and wherein the most distal end of the accommodation lumen is away from a linear reference line, in which the axis of the outer sheath at a distal portion of the proximal side tubular portion is positioned, in a direction perpendicular to the reference line.

19. The ultrasound catheter according to claim 18, wherein the outer sheath includes the proximal side tubular portion on the proximal side of the bent portion on the most proximal side; and an offset amount, which is a length from the linear reference line to the axis of the tubular position at a distal portion of the tubular position in the direction perpendicular to the linear reference line, is 5 mm to 30 mm.

20. The ultrasound catheter according to claim 18, wherein the bent portion of the outer sheath includes a first bent portion and a second bent portion, the first bent portion disposed distal of the proximal side tubular portion, the second bent portion disposed distal of the first bent portion and proximal of the tubular portion and bent toward a side opposite to the first bent portion, and wherein the axis of the outer sheath is bent at both the first bent portion and the second bent portion so as to define a bent angle of the first bent portion and the second bent portion.

* * * * *